US005756721A

United States Patent [19]
Eden et al.

[11] Patent Number: 5,756,721
[45] Date of Patent: May 26, 1998

[54] PURIFICATION OF POLYSACCHARIDES

[75] Inventors: James Eden, East Millstone; James Kasica, Whitehouse Station; Leo Walsh, Plainsboro; Morton W. Rutenberg, North Plainfield, all of N.J.; Norman Lacourse, Indianapolis, Ind.; Daniel Solarek, Belle Mead; Timothy G. Koubek, Clinton, both of N.J.

[73] Assignee: National Starch and Chemical Investment Holding Corporation, Wilmington, Del.

[21] Appl. No.: 297,673

[22] Filed: Aug. 29, 1994

Related U.S. Application Data

[63] Continuation-in-part of Ser. No. 832,838, Feb. 7, 1992, abandoned, and Ser. No. 995,301, Dec. 18, 1992, abandoned, which is a continuation of Ser. No. 642,095, Jan. 16, 1991, abandoned.

[51] Int. Cl.$^6$ .................... C07H 1/06; C07H 1/08
[52] U.S. Cl. .................. 536/127; 536/123.1; 536/124; 536/56; 536/102; 536/103; 536/114
[58] Field of Search .................. 536/127, 124, 536/123.1, 56, 102, 103, 114

[56] References Cited

U.S. PATENT DOCUMENTS

| | | | |
|---|---|---|---|
| 3,659,025 | 4/1972 | Halleck | 536/123.1 |
| 3,663,369 | 5/1972 | Morehouse et al. | 195/31 |
| 3,788,910 | 1/1974 | Stewart et al. | 195/11 |
| 3,849,194 | 11/1974 | Armbruster et al. | 127/29 |
| 3,853,706 | 12/1974 | Armbruster | 195/31 R |
| 3,910,820 | 10/1975 | Holt et al. | 195/31 |
| 3,974,034 | 8/1976 | Horn et al. | 195/31 R |
| 4,069,103 | 1/1978 | Müller | 195/4 |
| 4,109,075 | 8/1978 | Deaton | 536/1 |
| 4,119,435 | 10/1978 | Nakao et al. | 536/128 |
| 4,159,223 | 6/1979 | Baierl | 162/14 |
| 4,294,623 | 10/1981 | Hidaka et al. | 127/55 |
| 4,447,532 | 5/1984 | Coker et al. | 435/99 |
| 4,502,890 | 3/1985 | Urbanic | 127/46.2 |
| 4,511,654 | 4/1985 | Rohrbach et al. | 435/95 |
| 4,587,953 | 5/1986 | Rosene | 127/46.2 |
| 4,603,110 | 7/1986 | Morehouse et al. | 435/96 |
| 4,761,186 | 8/1988 | Schara et al. | 127/71 |
| 4,766,207 | 8/1988 | Deger et al. | 536/18.6 |
| 4,770,710 | 9/1988 | Friedman et al. | 127/29 |
| 4,826,619 | 5/1989 | Blaha et al. | 252/182.27 |
| 4,828,846 | 5/1989 | Rasco et al. | 426/18 |
| 4,871,571 | 10/1989 | Jensen et al. | 426/548 |
| 4,988,807 | 1/1991 | Christensen et al. | 536/127 |
| 4,990,605 | 2/1991 | Lueders | 536/18.5 |

FOREIGN PATENT DOCUMENTS

| | | |
|---|---|---|
| 0 342 156 | 11/1989 | European Pat. Off. . |
| 0 499 306 A1 | 8/1992 | European Pat. Off. . |
| 3 839 017 A1 | 5/1990 | Germany . |
| 43-16800 | 7/1968 | Japan . |
| 63-136374 | 6/1988 | Japan . |
| 221279 | 9/1924 | United Kingdom . |
| WO 89/04369 | 5/1989 | WIPO . |

OTHER PUBLICATIONS

Chemical Abstracts, vol. 85, No. 10, Sep. 6, 1976, Nakamura Tamotsu, et al., "Decolorizing Gum Arabic", p. 133, Abstract No. 65152a.

Chemical Abstracts, vol. 98, No. 8, Feb. 21, 1983, "Purification of Saccharified Solutions from Granular or Powdered Corn", p. 101, Abstract No. 55945r.

Whistler, Roy L., Bemiller, James N., Paschall, Eugene F., "Starch: Chemistry and Technology", Second Edition, Academic Press, Inc., 1984.

Anon., Type CPG LF 12X40 Mesh Granular Carbon, Tech. Bulletin of Calgon Carbon Corporation, pp. 1–2, Aug. 1987.

Anon., The Laboratory Evaluation of Granular Activated Carbons, Tech. Bulletin of Calgon Carbon Corporation, pp. 1–8, Jan. 1988.

Anon., Procedure for Filling and Defining Fixed Bed Adsorbers, Communication from Calgon Carbon Corporation.

*Primary Examiner*—John Kight, III
*Assistant Examiner*—Everett White
*Attorney, Agent, or Firm*—Karen G. Kaiser

[57] ABSTRACT

A steam-stripping process suitable for the removal of impurities from polysaccharides, including soluble starch hydrolysates, is disclosed herein. This process may be used in combination with other purification processes, such as ultrafiltration, ion exchange, treatment with activated carbon, as well as bleaching process. Soluble starch hydrolysates may also be purified by a combination of ultrafiltration or activated carbon treatment and bleaching. In these processes, the polysaccharide or the soluble starch hydrolysate produced is bland in flavor, free of off-odor, optionally, lighter or white in color and suitable for use in systems requiring these characteristics. Other purification process combinations which are disclosed for removal of undesirable flavors, odors and/or colors from polysaccharides include: 1) ultrafiltration and carbon treatment; 2) ultrafiltration and steam-stripping; 3) steam-stripping and carbon treatment; 4) ion exchange treatment and ultrafiltration; 5) ion exchange treatment and steam-stripping; and 6) ion exchange treatment and carbon treatment. A bleaching process may precede any of these processes. If ozone or a peroxide is employed, the bleaching step may follow any of these processes. Any of the processes may be combined with other processes disclosed herein to provide additional purification measures. The processes are particularly useful for purification of low molecular weight soluble polysaccharide hydrolysates, such as dextrins. These purified polysaccharides are used in improved foods, adhesives, pharmaceuticals and like products.

20 Claims, No Drawings

PURIFICATION OF POLYSACCHARIDES

This application is a continuation-in-part of Ser. No. 07/832,838 filed Feb. 7,1992, now abandoned, Ser. No. 07/995,301 filed Dec. 18, 1992, now abandoned, which is a continuation of Ser. No. 07/642,095 filed Jan. 16, 1991, now abandoned.

BACKGROUND OF THE INVENTION

This invention relates to processes for purifying polysaccharides by removing undesirable flavors, odors and/or colors. The processes may be selected to be compatible with soluble starch hydrolysates. The invention also relates to the use of these purified polysaccharides in food products, adhesives, cosmetics, household products such as cleaners and air fresheners, and in other applications wherein flavor, odor and/or color purity are required.

Filtration through activated carbon has been widely used in conversion processes for manufacturing monosaccharides, such as sugars and other sweeteners from starch. Syrups of glucose or dextrose and high fructose corn syrups that have been derived from starch are filtered through activated carbon to purify and decolorize the sweeteners. T. M. W. van Asbeck, et al., "The Evaluation of Activated Carbon in the Purification of Starch-Based Sweeteners", *Starch/Starke*, 33: 378–383 (1981). It is well-known in the art of sugar purification that a starch which has been only partially converted to sugar and contains significant quantities of starch hydrolysates or dextrins, will take on an undesirable gray color due to the emulsification of carbon fines by the starch hydrolysates.

Steam-stripping processes have been used to purify fats and oils and flavors and fragrances. The use of steam-stripping to purify polysaccharides has not been reported.

Processes known in the art for purifying starch using ultrafiltration are limited to the treatment of starch in insoluble form, whereby the insoluble starch may be readily separated from an aqueous wash.

Likewise, although many food ingredients have been subjected to bleaching steps during commercial processing to remove color (e.g. flour), the use of food grade bleaching agents to purify soluble starch hydrolysates by removing undesirable flavors and odors, as well as reducing color, has not been reported.

In spite of advances known in the art, there is an important industrial market for purified hydrolysates of starch having undesirable flavors, odors, and/or colors removed, as well as for new hydrolysates of starch and other polysaccharides having a bland taste, with little or no sweetness, that are available in the form of a non-hygroscopic powder. These new hydrolysates are useful as fat mimetic or fat replacers, and as carriers for synthetic sweeteners, flavors and fragrances, coloring agents and the like. They are also useful as spray-drying adjuncts for beverages (e.g., coffee or tea) and flavors and fragrances. They are useful as bulking agents, bodying and dispersing agents in foods such as coffee whiteners and as moisture binding agents in breads, pastry and meat products, particularly in low fat formulations of these foods. The unconverted starches, gums and other polysaccharides are also useful as thickeners, bodying agents and texture modifying agents in puddings, fruit products and frozen desserts and ice creams.

Starch in its native form, and starch hydrolysates that have been prepared by the acid, thermal, enzymatic and oxidative hydrolysis processes known in the art, each contain a variety of contaminants that contribute undesirable flavors (e.g., a "cereal" flavor), odors and colors to products such as foods and adhesives. Many other polysaccharides, such as food gums, in their native form also contain undesirable flavors, odors and colors. In addition, the presence of simple sugars or the presence of oligosaccharides may be undesirable in polysaccharide hydrolysates. Thus, there is a need for processes which remove such impurities from polysaccharide hydrolysates.

SUMMARY OF THE INVENTION

A steam-stripping process suitable for the removal of flavor and odor impurities from polysaccharides, including soluble starch hydrolysates, is disclosed here in. This process may be used alone or in combination with other purification processes, such as ultrafiltration, an ion exchange process or treatment with activated carbon, as well as with a bleaching process. Soluble starch hydrolysates may also be purified by a combination of ultrafiltration and bleaching or by a combination of activated carbon treatment and bleaching. In these processes, the polysaccharide (or the soluble starch hydrolysate) that is produced is bland in flavor, substantially free of off-odors, and, optionally, light or white in color and suitable for use in food, adhesive, or other systems requiring these characteristics.

The purified polysaccharides are generally useful in edible products. The purified starch hydrolysate products are useful in low or no fat spreads and margarines, frozen desserts, low fat sour cream and cheese, fortified skim milk, white or cream sauces, including alfredo sauce and other cheese-containing sauces, frozen, dry, jarred, or canned prepared sauces, cream soups, low fat cheese spreads, coffee whiteners, dry cocoa mixes and other drink mixes, whipped dairy toppings, artificial sweeteners, puddings and pie fillings including low fat puddings and pie fillings, cakes, baked goods and pastries, low fat baked goods, cakes and pastries and other dairy and low fat products. The purified polysaccharides, including the starch hydrolysate products, are also useful in adhesives, cosmetics, household products, pharmaceutical products (such as binders and diluents), and the like.

The steam-stripping process disclosed herein for removal of undesirable flavors and odors from soluble polysaccharides, comprises the steps:
1. dispersing the polysaccharide at 1 to 40% solids in an aqueous media,
2. feeding the polysaccharide dispersion into a steam-stripping apparatus,
3. applying a current of steam to remove undesirable flavors, and odors,
4. separating the steam bearing the undesirable flavors and odors from the polysaccharide, and
5. recovering the purified, soluble polysaccharide.

Where an insoluble polysaccharide product is desired, the polysaccharide is slurried in water before steam-stripping and the process is carried out under a vacuum at temperatures below the temperature where the polysaccharide becomes fully dispersed and/or water-soluble (e.g., the gelatinization temperature of starch).

This process optionally includes the additional step of bleaching the polysaccharide.

The following additional purification process combinations are disclosed herein for removal of undesirable flavors, odors and/or colors from polysaccharides:
1. Ultrafiltration and carbon treatment;
2. Ultrafiltration and steam-stripping;
3. Steam-stripping and carbon treatment;
4. Ion exchange treatment and ultrafiltration;

5. Ion exchange treatment and steam-stripping; and
6. Ion exchange treatment and carbon treatment.

These processes may be carried out in any order. A bleaching process may precede any of these processes. If ozone or a peroxide bleaching agent is employed, the bleaching step may follow any of these processes. Any of the processes may be combined with other processes disclosed herein to provide additional purification measures.

When steam-stripping, ultrafiltration, or bleaching is employed, the polysaccharide raw material may be either soluble or insoluble in water. When the activated carbon treatment or ion exchange treatment is employed the polysaccharide raw material should be at least partially soluble (i.e., dispersed), preferably soluble (i.e., fully dispersed) in water. All of the processes of this invention are particularly useful for purification of soluble polysacharide hydrolysates, such as dextrins.

DESCRIPTION OF THE PREFERRED EMBODIMENTS

The processes of this invention may be carried out on any polysaccharide raw material, except that the carbon treatment and ion exchange is limited to polysaccharides in a water soluble (e.g., gelatinized starch or dispersed gum) form.

As used herein, "soluble" means that the polysaccharide in powdered form may be readily hydrated and dispersed in water or other aqueous medium to provide a polysaccharide solution in the form of a complex colloidal dispersion, rather than a true molecular solution. Some polysaccharides do form a true molecular solution (e.g., pectin, high D.E. dextrins). It may be necessary to heat the polysaccharide to fully hydrate and disperse it.

The term "polysaccharide" as used herein refers to starches, gums, dextrins, celluloses, and heteropolysaccharides, and derivatives thereof, hydrolysates thereof, crosslinked products thereof and combinations thereof.

As used herein, the term "dextrin" refers to glucose polymers having a dextrose equivalent (D.E.) of less than 20. Dextrins preferred for use in the process of this invention have a D.E. less than or equal to 10, preferably a D.E. of less than 5, most preferably a D.E. of 0.5 to 5. The term "dextrose equivalent" refers to the reducing power (or the reducing sugar content) of starch hydrolysates calculated as dextrose (dextrose or glucose has a D.E.=100) on a dry weight basis. Dextrins having a high D.E. have lower molecular weights (are more highly converted) than those having a low D.E.

Also preferred for use as raw materials in the processes of this invention are starch hydrolysates, including fluidity starches having a water fluidity (WF) value of 30 to 85, prepared by acid, enzyme (e.g., alpha-amylase) or oxidative conversion processes known in the art; enzymatically debranched starches comprising up to about 85% short chain amylose; and dextrins (pyrodextrins) derived by subjecting starch to a dry, thermal degradation process or to an acidic, dry, thermal degradation process to yield a dextrin having an anhydrous borax fluidity (ABF) value of 8 to 1. (A viscosity of a dextrin having an ABF of 8 is roughly equivalent to the viscosity of a 70 WF acid-converted starch.) The "ABF value" is the ratio of the amount of water to the amount of dextrin when the latter is cooked for five minutes at 90° C. (195° F.) with 15% of borax on the weight of dextrin, so as to provide a dispersion having a viscosity, when cooled to 25° C. (77° F.), of 70 centipoises. Higher ABF values are associated with higher molecular weight dextrins.

The debranched starches suitable for use herein are described in U.S. Pat. No. 4,971,723, issued Nov. 20, 1990 to Chiu, which is hereby incorporated by reference. In addition to the partially debranched starches disclosed therein, fully debranched starches (i.e., containing about 85% to 100% short chain amylose) that have been treated with an endo-alpha-1,6-glucanohydrolase, such as pullulanase, may be used in the processes herein.

Where a low viscosity starch is desirable, a starch, such as waxy maize, which has been converted to a Water Fluidity (WF) of up to about 60 is preferred. Water Fluidity is an empirical measure of viscosity on a scale of 0–90, wherein fluidity is the reciprocal of viscosity.

Other low molecular weight (e.g., a molecular weight of about 500 to 500,000) polysaccharides useful herein include degraded or depolymerized food gums, and other heteropolysaccharides, hemicelluloses, cellulosic materials, food fibers and dextrans. "Food fibers" refers to those polysaccharides from plants sources that are neither starches, celluloses, gums nor any other polysaccharide specifically mentioned herein. Any of these polysaccharides may be degraded by any method known in the art, preferably by treatment with acid or enzyme. Suitable gums include guar gum, locust bean gum, carob seed gum, tamarind seed gum, konjac gum, xanthan gum, alginates, agar, pectin, gum arabic and carrageenan. Suitable cellulosic materials include cellulose, alpha-cellulose, microcrystalline cellulose, carboxymethylcellulose, methylcellulose, hydroxymethylcellulose, and hydroxyethylcellulose.

If the polysaccharide is to be modified prior to purification by the processes herein, such modification may be carried out by any method known in the art and in any combination thereof. In a preferred mode, conversion, derivatization and crosslinking modifications are carried out on the polysaccharide in an insoluble form (e.g., granular starch). While modifications may be carried out after purification, it is generally desirable to complete modifications first so that reagents, salts, and other reaction by-products may be removed during purification.

These modifications, such as derivatization of starch, cellulose, heteropolysaccharides and gums to form ester- or ether-linked substituents along the polysaccharide backbone, are well known in the art and described in publications such as M. W. Rutenberg, "Starch and Its Modifications" P. 22: 36, in *Handbook of Water-Soluble Gums and Resins*, R. L. Davidson, editor, McGraw Hill, Inc., New York, N.Y., 1980.

In a preferred embodiment wherein the polysaccharide is starch, the starch is treated with octenylsuccinic acid anhydride (OSAA) to form a starch ester derivative containing from 0.25 to 3.0%, by weight, of octenylsuccinate prior to purification by steam-stripping, ultrafiltration, carbon treatment or ion exchange treatment or a combination thereof. The OSAA treated polysaccharides are preferably not bleached because the bleaching agents can remove octenylsuccinate substituents from the polysaccharide at pH extremes. Bleaching may be carried out at moderate pH values.

Steam-stripping

In this process, a slurry or a dispersion of polysaccharide is permitted to flow down a column packed with inert solid support against a current of culinary-grade steam. Although a counter current of steam is preferred, any method of passing steam through the polysaccharide slurry or dispersion may be used. The steam volatilizes and carries away many of the flavor compounds, and their precursors, that are known to cause off-flavors (e.g., corn-like, beany, musty, burnt, earthy, etc.) in polysaccharides. The steam carrying its complement of flavor compounds is removed from the top of the column and condensed. The purified polysaccharide slurry or dispersion is recovered from the steam, preferably at the bottom of a column. The process is preferably continuous, but may be performed in batch operations.

To maintain an efficient column purification process, the steam must be maintained as the continuous phase and "flooding" of the column by excess feed material must be avoided. Various types of suitable process conditions and equipment designs are known in the art and described in publications such as *Perry's Chemical Engineers' Handbook*, 6th Edition, 1984, McGraw Hill Book Company, New York, N.Y., Chapter 18.

Although a variety of temperature and pressure ranges for the feed, the steam and the column, or other suitable apparatus, may be selected to complement the polysaccharide raw material and the intended product, conditions are broadly determined by whether the product is to be in water-soluble or insoluble form. For the water-soluble product, column steam pressure may range from 5 to 300 psig, preferably 10 to 40 psig, feed temperature from 55° to 200° C., preferably 80° to 200° C., and steam temperature from 55° to 200° C., preferably 115° to 140° C. For the insoluble product, column pressure under vacuum may range from −5 to −14.5 psig, preferably −10 to −14.5 psig, feed temperature from 25° to 80° C., preferably to 55° to 80° C., with a steam flow rate of 15 to 2,500 lbs/hour/ft$^2$, preferably 150 to 1,500 lbs/hour/ft$^2$. The soluble product may be steam-stripped at atmospheric pressure. The insoluble product, when it is a starch, must be steam stripped at a temperature below its gelatinization temperature. Typically, it is steam-stripped at less than atmospheric pressure, preferably under a −5 to −14.5 psig vacuum, so as to avoid cooking the starch or gum and producing a fully dispersed or a soluble product.

The rate of feed may range from 0.03 to 3.75 gallons/minute/square foot of cross-sectional area of the apparatus (gal/min/ft$^2$), preferably about 3.0 gal/min/ft$^2$, for a 1 to 40% solids slurry or dispersion. Suitable feed rates will vary depending upon the scale of the operation (e.g., laboratory vs. manufacturing scale), the packing materials, steam temperature and pressure and the viscosity and other rheological characteristics of the polysaccharide raw material in a slurry or dispersion. For example, on a laboratory scale apparatus using a glass column ranging from 10.2 cm (4") in diameter× 91.4 cm (36") in height to 15.2 cm (6") in diameter×304.8 cm (120") in height, a rate of feed from 0.03 to 1.0 gal/min/ft$^2$ is suitable.

The viscosity of the feed material should be adjusted to less than 300 cps at the operating temperature of the column, preferably less than 100 cps at the column temperature, and most preferably 1 to 10 cps at column temperature. At a flow rate of about 3.0 gal/min/ft$^2$, and with steam at 80° to 200° C. and 10 to 40 psig, the feed solids content of a soluble starch hydrolysate dispersion is preferably 15 to 25%. For a higher molecular weight, more viscous soluble polysaccharides, such as fully dispersed high amylose corn starch or locust bean gum, the solids content of the feed is preferably 10 to 20% at a feed flow rate of 2.0 gal/min/ft$^2$ and steam at 80° to 200° C. and 10 to 40 psig. The practitioner will recognize that lower flow rates and lower percentages of solids in the feed will not be economical, whereas higher flow rates and solids may exceed the capacity of the steam-stripping apparatus for removal of flavors and odors. High solids may create a feed viscosity that is too high to run on the apparatus. Conditions suitable for a variety of polysaccharides are described in the examples, below.

The apparatus may be selected from a variety of designs known in the art, preferably vertical column designs that permit gravity feed of the slurry or dispersion against an upward flow or countercurrent of steam. The apparatus must be constructed of inert materials that will not contribute off-flavors, odors or colors or other contaminants to the polysaccharide. Packing materials for the apparatus may be selected from any of a variety of commercially available proprietary designs. A column apparatus is preferably packed with packing materials that provide high contact surface area and permit high flow rates (e.g., glass beads, stainless steel rings or other stainless steel packing material). The steam-stripping apparatus may be linked to an apparatus for cooking or drying the polysaccharide or to an apparatus for carrying out bleaching steps or other purification steps. When the polysaccharide is used in an edible product, a source of culinary steam, or a means for removing odors, colors and flavor contaminants from other types of steam, is an essential element of the apparatus used in this process. Suitable apparatus designs are described in the examples, below.

The steam-stripping process may be carried out in conjunction with other purification processes described herein, including ultrafiltration, treatment with activated carbon, bleaching and ion exchange treatment, or any combination thereof. If bleaching is carried out after steam-stripping, the bleaching agent must be selected such that it is consumed by the process and no residual reagent remains to create off flavors. All other purification processes may be carried out in any order, before or after steam-stripping.

In a preferred mode, steam-stripping is combined with ion exchange treatment or ultrafiltration to remove salts and other low molecular weight non-volatile contaminants as well as volatile off-flavors and odors.

In another preferred mode, bleaching is carried out followed by steam-stripping to remove color, flavor and odor contaminants and their precursors.

Bleaching

In this process, a slurry or dispersion of polysaccharide is brought into contact with selected bleaching agents to remove off-flavors, odors and/or colors. Process conditions are selected to be mild enough to avoid any significant degradation of the polysaccharide (i.e., oxidative conversion to a lower molecular weight) but strong enough to improve flavor, odor, and, optionally, color of the polysaccharide. The bleaching agents useful herein include chlorite salts, such as sodium chlorite, hypochlorite salts, such as calcium or sodium hypochlorite, peroxides, such as hydrogen peroxide or peracetic acid, persulfate salts, such as sodium, potassium or ammonium persulfate, permanganate salts, such as potassium permanganate, chlorine dioxide, and ozone. Bleaching is carried out in conjunction with other purification processes.

To avoid polysaccharide degradation, the polysaccharides are treated with a concentration of bleaching agent that is at least at a magnitude of $10^{-1}$ times less than the limits set by the U.S. Food and Drug Administration for chlorine (as sodium hypochlorite) used in degrading starch to produce modified food starch (i.e., a maximum of 5.5% chlorine on a starch dry weight basis is permitted).

Polysaccharides are preferably treated with 0.1 to 0.5%, on a polysaccharide dry weight basis, of sodium chlorite at a solution pH of 3.0 to 4.5 and a temperature of 25° to 95° C. for a period of time effective to remove undesirable flavors and odors and create a product that is lighter in color. Depending on temperature, level of contamination and chlorite concentration, the requisite time may range from about 10 or 15 minutes to 1 to 3 days.

In a preferred embodiment, a dispersion of about 14 to 25% starch hydrolysate is treated with 0.1 to 0.5%, preferably 0.19%, sodium chlorite, on a starch dry weight basis, at a pH of 3.0 to 4.5 and a temperature of less than 100° C., preferably 80° to 95° C., for 1.5 hours. This reaction will consume all active chlorine and bleach the starch to yield a light-colored or a white product, having less intense brown, tan or yellow colors. The same reaction may be carried out at 25° C. for about 12 to 18 hours. The bleaching is carried out in a Teflon® coated vessel or in some other vessel constructed with inert materials in all bleaching agent contact surfaces. Stainless steel and other metals are generally not suitable for use in the bleaching process if a strong oxidant, such as sodium chlorite, is used. Peroxides may be used in stainless steel vessels.

In a preferred embodiment the bleaching process is carried out before steam-stripping, ultrafiltration, carbon treatment or ion exchange treatment, or a combination thereof, so as to remove any residual bleaching agent from the polysaccharide.

In another preferred embodiment, the bleaching agent is selected from the peroxide agents, ozone and any other bleaching agent that is consumed by the process without creating undesirable by-products or contaminants. In this embodiment, the bleaching process may be carried out before or after or in between the other purification processes, alone or in combination.

Ultrafiltration

The ultrafiltration process employs a semi-permeable membrane having a minimum molecular weight cut-off (MWCO) of about 1,000 to separate a bleached polysaccharide slurry or dispersion from low molecular weight contaminants (i.e., a molecular weight of less than 1,000) so as to improve flavor, odor and/or color qualities of the polysaccharide. The "MWCO" is the molecular weight of a globular solute at which the solute is 90% rejected by the membrane. The slurry or dispersion is fed or pumped through an ultrafiltration apparatus at a pressure less than 100 psig to avoid breakage of polymer membranes while insuring adequate amounts of separation and an economical flow rate. Pressures greater than 100 psig can be used with ceramic or metallic membranes. The contaminants pass through the membrane, while the polysaccharides are retained by the membrane so as to effect their separation. The polysaccharide slurry or dispersion is collected and further purified or dried.

In a preferred embodiment, the ultrafiltration process is carried out while maintaining a constant amount of feed water (i.e., as a diafiltration process) so as to provide additional, continuous polysaccharide washing during filtration. The apparatus comprises a feed tank for holding the dispersion or slurry with agitation, a pump for moving the feed past the membrane, a means for supplying deionized water, a means for removing the permeate and a means for removing the retentate. Any ultrafiltration apparatus known in the art may be used herein, provided that it is equipped with a suitable membrane that can effectively separate lower molecular weight flavor, odor and/or color contaminants.

Suitable membranes include conventional ultrafiltration membranes having flat, tubular, spiral, hollow fiber or other configurations. The membrane may be constructed from cellulose derivatives (such as cellulose acetate), polyamide, fluorocarbon, polysulfone and other suitable materials.

In a preferred embodiment, a Prolab Ultrafiltration Unit (obtained from Millipore Corporation, Bedford, Mass.) is equipped with an Amicon® 100,000 MWCO polysulfone filter (obtained from Amicon Division, W. R. Grace & Company, Beverly, Mass.).

For flavor improvement of soluble polysaccharide hydrolysates, a 30,000 MWCO filter is preferably used, and a 10,000 MWCO filter is most preferably used. A 1,000 MWCO filter also may be used. Better polysaccharide yield (e.g., 88% versus 84%) is obtained with 30,000 or 10,000 versus 100,000 MWCO filters. Higher flux rates (i.e., rates of permeate flow through the membrane) are possible with 100,000 or 30,000 versus 10,000 MWCO filters (e.g., 25 ml/min versus 20 mls/min). In general, a membrane having a MWCO of about $10^{-1}$ times less than the molecular weight of the polysaccharide is preferred (e.g., soluble starch hydrolysates used as fat mimetic in foods [having average molecular weights of about 300,000 to 750,000] are preferably filtered with a 30,000 MWCO membrane). Thus, the practitioner may be guided by the molecular weight of the polysaccharide that will be filtered in selecting an appropriate membrane. Other polysaccharide characteristics such as molecular shape and tendency to aggregate will also guide the practitioner.

To complete purification of the polysaccharide, the ultrafiltration process may be combined with a bleaching process, as disclosed herein, or with steam-stripping, ion exchange or carbon treatment, or a combination thereof. Bleaching is preferably carried out before ultrafiltration, but the other processes may be carried out in any order.

Ion Exchange Treatment

An ion exchange treatment may be used in combination with the steam-stripping and carbon treatment purification processes disclosed herein, with or without an additional bleaching step, to remove off-flavors, odors and/or colors from polysaccharides. These processes may be carried out in any order. While ion exchange treatment may be used in conjunction with ultrafiltration, it is typically used in lieu of ultrafiltration. In the ion exchange treatment a slurry or a dispersion of the polysaccharide is brought into contact with suitable resins such that undesirable salts, colors and other contaminants are removed from the polysaccharide slurry or dispersion.

In a preferred embodiment the polysaccharide slurry or dispersion is treated by feeding it into a column packed with an anion ion exchange resin and then feeding it onto a column packed with a cation exchange resin.

An "anion exchange resin" is a solid polymeric material that has a positively charged matrix and exchangeable negative ions or anions. A "cation exchange resin" is a solid polymeric material that has a negatively charged matrix and exchangeable positive ions or cations.

In another preferred embodiment, only one type of resin is used in the process. Where only one type of resin is used, anion exchange resin is preferred. Suitable anion exchange resins include epoxy resin-based polymers (e.g., an epoxy-amine polymer). Suitable cation exchange resins include acrylic acid copolymers (e.g., an acrylic-divinylbenzene copolymer); and sulfonic acid-containing copolymer compositions of styrenedivinylbenzene. A variety of suitable resins of the anion exchange variety, and conditions for their use and preparation are disclosed in U.S. Pat. No. 4,988,807, issued Jan. 29, 1991, to Christensen, et al., which is hereby incorporated by reference.

The flow rate of the process and the size of the column to be used are a function of: the amount of undesirable material in the polysaccharide, the resin being used, and the amount of undesirable material to be removed. The exact values for each of these parameters must be adjusted to meet the desired results. In general, the amount of removal of undesirable material is a function of the contact time of the polysaccharide slurry or dispersion with the resin, with longer contact times given to more highly purified polysaccharides. For a given amount of removal of undesirable material, the required contact time can be achieved by numerous combinations of flow rate and column size. Typically, the flow rates range from about 0.001 to about 10.0 gallons per minute per square foot of resin cross-section ($gal/min/ft^2$), preferably from about 0.1 to about 2.0 $gal/min/ft^2$.

The acceptable level of undesirable material in the polysaccharide remaining after treatment, or, alternatively, the amount of undesired material to be removed from the polysaccharide during treatment will depend on the specific end use for which the polysaccharide is intended. Thus, an effective level of removal of the undesired material will be dictated by specific consumer or industrial need requirements of the final product and, as such, will vary from final product to final product.

The process is typically operated at elevated temperatures of about 50° to about 100° C. For certain polysaccharides, such as methylcellulose which may precipitate or gel at elevated temperatures, ambient temperatures of about 15° to about 35° C. are effective. This gelling or precipitation could cause the column to be blocked; thereby, inhibiting the flow of the aqueous solution through the column. Where other polysaccharides, especially soluble or fully dispersed polysaccharides (e.g., gelatinized starch) are used, elevated temperatures are preferred. Elevated temperatures are required for effective treatment of gelling starches and gelling starch hydrolysates.

Several factors may affect the efficiency of the removal of undesirable material from the polysaccharide containing such undesirable material, with the main concerns being the viscosity, pH, and salt content of the polysaccharide slurry or dispersion. The polysaccharide slurry or dispersion should not be so viscous that reasonable flow rates, as described herein, cannot be achieved without resorting to excess column pressures to force the slurry or dispersion through the column. Typically accepted pressures to aid in the process are from about 1 to about 300 psig, preferably from atmospheric pressure to about 80 psig.

A preferred embodiment for purifying polysaccharides using ion exchange treatment in conjunction with carbon treatment and bleaching is disclosed in the examples, below. Depending upon the polysaccharide raw material characteristics and the requirements of the end use application, the practitioner may readily select resins and conditions known in the art to optimize the ion exchange step within the polysaccharide purification process.

Carbon Treatment

Any carbon purification treatment known in the art may be used in combination with the steam-stripping, ion exchange, ultrafiltration and bleaching processes herein, provided that emulsification of carbon fines by the polysaccharide is controlled such that a gray color does not develop in the carbon-treated polysaccharides. This gray color is created by the emulsified carbon fines and neither bleaching nor the other purification steps disclosed herein can remove this color.

The activated carbon treatment described hereafter may be used alone or in combination with the steam stripping, ion exchange, ultrafiltration, and bleaching processes herein. The treatment is particularly useful for starch, maltodextrin and dextrin. The starch is preferably degraded to form hydrolysis products having dextrose equivalents (DE) of 20 or less, preferably 5 or less. The hydrolysis products may be formed from starch by acid, heat or enzyme degradation, or a combination thereof.

In a preferred embodiment, a starch hydrolysate is bleached, steam-stripped and treated with activated carbon to remove objectionable flavors, odors and colors. An apparatus and process for carbon treatment suitable for use in this embodiment are described in the examples, below.

The activated carbon treatment process requires that the polysaccharide be at least partially solubilized (i.e., dispersed) before passage through the column. Starch, maltodextrin or dextrin may be dispersed by any method known in the art, preferably by heating it in water for a period of time sufficient to gelatinize the starch, maltodextrin or dextrin, or by treatment with alkali to disperse the starch, maltodextrin or dextrin. The starch, maltodextrin or dextrin may be pregelatinized, dried and then rehydrated in cold or hot water to form a dispersion. Jet-cooking, drum-drying, spray-drying and steam injection atomization processes, and other processes known in the art may be used to gelatinize these polysaccharides. The practioner will recognize that different processes known in the art may be used to solubilize polysaccharides other than starch, maltodextrin and dextrin. In a preferred embodiment, the starch is slurried in water and jet-cooked at approximately 300° F. (149° C.) to instantaneously and thoroughly disperse the starch.

The conversion of starch to a dextrin or to some other, lower molecular weight form of starch, may be achieved by standard heat, acid or enzyme (e.g., alpha-amylase) conversion techniques which are well known in the art. Starches, dextrins and maltodextrins may be derivatized to add ether or ester substituents. Each of these processes should be carried out prior to treatment with activated carbon so as to permit removal of any contaminants added during the modification steps.

In addition to the step of providing a dispersed polysaccharide, the process herein requires the following steps:

1) passing the dispersed polysaccharide through at least one column packed with pre-washed, granular, activated carbon at a flow rate of 0.1 to 20.0 bed volumes/hour, which column has been loaded with wetted carbon granules, back-washed and pre-heated; and 2) recovering the polysaccharide dispersion in a form which is substantially free of carbon fines, as evidenced by the absence of a gray color.

To prevent the emulsification of carbon fines, it is essential to remove the fines by pre-washing the carbon, wetting the carbon before and during the column preparation, carefully loading the column so as not to generate additional carbon fines and extensively flushing the column to wash any fines out of the bed. During treatment, disruption of the bed must be avoided and additional back-washing steps may be needed to purify a column bed which has been disrupted.

Granular, rather than powdered, activated carbon must be used in the column. Granular carbon having a high degree of hardness and a 12×40 mesh size (U.S. Sieve series) is preferred. The activated carbon must be loaded into a column or otherwise immobilized in order to reduce carbon fine generation. If the carbon granules are mixed into a polysaccharide dispersion and then filtered out, the carbon treated polysaccharide will contain carbon fines and be characterized by an undesirable gray color. Likewise, while prewashing the carbon, excess agitation should be avoided so as to reduce generation of fines.

After prewashing the carbon, the carbon should be wetted and should remain wet during column loading and operation so as to avoid forming air bubbles and trapping the air bubbles within the column. The air bubbles reduce the absorptive capabilities of the carbon. In a preferred embodiment the carbon is wetted in water for 24 hours. In another preferred embodiment the carbon may be boiled in water for 2 hours to wet the carbon and liberate fines which can be decanted from the wetted carbon.

The wetted carbon should be transferred into a column in a wet form to avoid generation of new fines and dust. Additionally, if the water level drops below the height of the carbon in the column, carbon fines appear when the carbon is resubmerged in water.

To complete the preparation of a column suitable for treating polysaccharides, the column containing the carbon must be back-flushed. To back-flush the column, water is pumped from the bottom of the column to the top against the force of gravity, carrying upward the smaller carbon particles. This movement of water upward through the column stratifies the particles by size, with the larger particles falling to the bottom and the fines being carried up and out of the top of the column. This classification of the carbon by particle size results in an efficient configuration for treatment of polysaccharides. The smaller particles have more surface area to absorb impurities in the polysaccharide dispersion as the dispersion is applied to the top of the column.

So long as the column can be loaded as described herein to minimize the generation of carbon fines, any size or type of column may be used herein. The flow rate, pump size, valves, volume of wash water, temperature, pH and other aspects of the carbon treatment process will vary depending upon several variables, including the size of the column, the nature of the material to be purified and whether the process is continuous or batch. About 0.1 to 20% carbon, preferably 1 to 7% carbon, on a dry weight basis may be used to treat any given amount of starch.

The rate at which the carbon treatment may be conducted depends upon how much purification is required, together with the variables listed above. While rates of 0.1 to 20.0 bed volumes/hour may be employed, the practitioner will recognize that only limited amounts of purification can be accomplished at the higher rates. In a preferred embodiment a treatment rate of 0.2 to 3.0 bed volumes/hour is selected.

The process may be carried out at any temperature so long as the polysaccharide remains substantially dispersed and does not retrograde or gel before or during passage through the column. A change in temperature also will affect the adsorptive capability of the carbon. The process may be carried out at temperatures ranging from 0° to 100° C., preferably about 20° to 30° C. for non-retrograding polysaccharides and about 60° to 100° C. for retrograding polysaccharides.

Because the nature of activated carbon may change with a change in pH, the pH of the dispersed polysaccharide should be monitored throughout the treatment so as to avoid loss of purification capacity. The carbon may change the pH of the material being treated and pH adjustment of the treated product may be required. In a preferred embodiment, the pH is maintained between 3 and 8 during treatment.

The polysaccharide dispersion may be passed through more than one activated carbon column. In a preferred embodiment, a 14–32% dispersion of a dextrin at pH of 4 to 7 is treated at 60°–95° C. by passing the dispersion through a 40" glass column, having a 2" internal diameter, which has been packed with granular activated carbon as described above. The dispersion is passed through the column at a flow rate of 0.2 to 3.0 bed volumes/hour. About 1 to 7% carbon on a dry weight basis is used to treat the dextrin on a dry weight basis.

Foods, Pharmaceuticals and Adhesives

The organoleptic qualities of polysaccharide-containing edible products may be improved by substituting the purified polysaccharides of this invention for the conventional polysaccharides (or other components) of the edible product in amounts from about 0.05 to 100%, preferably 1 to 50%, by weight, of the edible product. The degree of flavor, odor and/or color improvement observed is proportional to the percent of polysaccharide used in the edible product, to the absence of strong flavors and odors in the edible product, and to the whiteness of color normally associated with the edible product.

Thus, the polysaccharides that have been purified by the processes of this invention are preferably used to formulate the following types of foods:

low or no fat spread, margarine, frozen dessert, low fat sour cream, low fat cheese, fortified skim milk, white sauce, cream sauce, alfredo sauce, cheese sauce, frozen sauce, canned sauce, salad dressing, cream soup, soup, cheese spread, coffee whitener, dry cocoa mix, whipped dairy topping, artificial sweetener, pudding, pie filling, cake, baked goods, pastry, low fat baked goods, low fat salad dressing, and low fat dairy products.

Among the low or no fat foods (i.e., foods containing essentially no fat or no more than 30% of the fat normally associated with the food), starches that have been degraded with acid, heat, oxidative or enzyme treatment, or a combination thereof, to yield a starch hydrolysate having a D.E. of less than 10, preferably 0.5 to 5, or an ABF value of 8 to 1, or containing at least 60% short chain amylose after debranching, and then purified as described herein, are preferred.

In particular, those starch hydrolysates that have been subjected to:

1) bleaching and steam-stripping;
2) bleaching, steam-stripping and carbon treatment; or
3) bleaching, ultrafiltration and steam-stripping are preferred for use in low-fat foods as a fat mimetic or a fat replacer.

In another preferred embodiment, the polysaccharides purified by the processes herein are used in foods, adhesives, or pharmaceuticals, as thickeners, bodying agents, binders, coatings, carriers or dispersants, nutrients, encapsulants, emulsifiers, stabilizers, fillers or diluents.

EXAMPLE 1

This example illustrates the bleaching of soluble starch hydrolysates to remove undesirable flavors, odors and/or colors.

An alpha-amylase-converted, pregelatinized tapioca maltodextrin (having a D.E. of less than 5) was mixed at 35% solids in deionized water and the mixture was heated to 80°–90° C. to disperse the starch. The dispersion was jet-cooked (in a jet-cooker obtained from National Starch and Chemical Company, Bridgewater, N.J.) at 120°–130° C. (250°–265° F.) and transferred to a non-metallic jacketed tank.

The pH of the dispersion was lowered to 3.5 with hydrochloric acid and the temperature was held at 80°–95° C. during treatment with an aqueous solution of food grade sodium chlorite at 0.19% sodium chlorite on a dextrin dry weight basis. The bleaching continued with mixing until the residual chlorite was consumed (visually, bleaching was completed in 3–10 minutes). In a 25–35 gallon batch, the bleaching agent was completely consumed in 1 to 1.5 hours as measured by a colorimetric potassium iodide spot test. (In this test, any residual bleaching agent present in a test sample of the starch dispersion will oxidize the potassium iodide reagent to yield iodine at a pH of 3.5. The iodine then forms a complex with starch that is blue in color.) In batches containing excess chlorite, a dilute sodium bisulfite solution was used to neutralize the bleaching agent. Following bleaching, the pH was raised to 6.5 with sodium hydroxide.

EXAMPLE 2

Undesirable flavors and other contaminants were removed from an alpha-amylase enzyme-converted, pregelatinized tapioca maltodextrin (having a D.E. less than 5) using a steam-stripping process, alone and in combination with the bleaching process of Example 1.

In the steam-stripping process a stainless steel column measuring 6 inches (15 cm) in diameter and 4 feet (1.22 meter) in height was packed with 0.7 inch (1.78 cm) in diameter 316 stainless steel rings (obtained from Nutter Engineering, Tulsa, Okla.). In subsequent trials a high surface area, structured packing material supplied as cylindrical pieces measuring 6 inches (15 cm) in diameter and 8.5 inches (21.6 cm) in height (Montz B1-400, 316 stainless steel packing, obtained from Nutter Engineering, Tulsa, Okla.) was used in lieu of the rings. In subsequent trials a 10 foot column was used in lieu of the 4 foot column.

The bottom of the column was fitted with a 0.062 inch (0.16 cm) thick stainless steel plate, perforated with 0.122 inch (0.31 cm) holes, and with a bottom dome connected to a steam condensate trap (TLV model SS3V, with a #21 orifice, obtained from TLV America, Charlotte, N.C.) and a starch outlet. The stripping steam (generated from deionized water) entered a fitting at the side of the bottom dome of the column at a maximum pressure of 60 psi with a maximum flow of 35 pounds/hour. The steam flowed upward through the column, countercurrent to the starch flow. The steam exited the column through a ½ inch (1.27 cm) pipe fitting at the side of the dome at the top of the column. Constant steam pressure in the column was maintained with a diaphragm back pressure valve (Fisher model 98L, obtained from Fisher Controls, Marshalltown, Iowa).

The column and all piping used in the steam-stripping apparatus were insulated to prevent heat loss.

The dispersed starch was fed directly, under pressure, from the column through ¼ inch (0.64 cm) stainless steel tubing into the nozzle of a spray-dryer. The spray-dryer was a 4 feet (1.22 meter) in diameter Niro laboratory scale spray-dryer with air inlet temperatures of 200°–250° C. and outlet temperatures of 115°–120° C. After spray-drying, the starch had a moisture content of about 4–5%.

The steam-stripping process produced a purified tapioca maltodextrin having improved flavor and organoleptic qualities in aqueous dispersions compared to an untreated control (an alpha-amylase enzyme-converted pregelatinized tapioca dextrin having a D.E. of less than 5). These improvements were observed irrespective of whether the dextrin had been bleached. (See Table II.) Similar improvements were observed in samples prepared under each of the operating conditions listed in Tables I and II, below. In general, steam-stripping flavor improvements were most significant at starch dispersion solids of at least 14% (e.g., a taste panel preferred Batch Nos. 11 and 12 that were stripped at solids of 25 and 14%, respectively, over Batch No. 13 at 10% solids). More significant improvements were also observed in samples that were steam-stripped at the higher ranges of temperature and higher steam flow rates that were tested in the steam-stripping apparatus designs described above.

Tapioca dextrins that had been bleached and steam-stripped were preferred (had a blander flavor and no gray, brown or tan off-colors) over a control dextrin and a control dextrin that had been only steam-stripped.

TABLE I

Steam-stripped Starch Hydrolysates

| Run: | Converted Tapioca Dextrin[a], 4 foot column, ring packing, spray-dried[b] | | | | | | Oxidized Waxy Maize Fluidity Starch[c] 10 foot column, B1-400 packing[d], spray-dried[b] | | | | Converted Tapioca Dextrin[a,e] 10 foot column, B1-400 Packing[d], spray-dried[b] | | | | |
|---|---|---|---|---|---|---|---|---|---|---|---|---|---|---|---|
| Batch | 1 | 2 | 3 | 4 | 5 | 6 | 7 | 8 | 9 | 10 | 11 | 12 | 13 | 14 | 15 |
| Feed Solids (%) | 24 | 24 | 30 | 30 | 30 | 20 | 27 | 27 | 27 | 27 | 24 | 14 | 10 | 14 | 12 |
| Feed Rate (ml/min) | 225 | 225 | 200 | 200 | 120 | 125 | 125 | 125 | 125 | 125 | 225 | 225 | 225 | 335 | 335 |
| Steam Flow (lb/hour) | 30 | 25 | 30 | 35 | 30 | 30 | 30 | 30 | 20 | 20 | 30 | 30 | 30 | 30 | 30 |
| Column Temp °C. (°F.) | 190 (275) | 130 (268) | 190 (275) | 190 (275) | 190 (275) | 190 (275) | 190 (275) | 120 (245) | 190 (275) | 120 (245) | 190 (275) | 190 (275) | 190 (275) | 190 (275) | 190 (275) |
| pressure (psig) | 30 | 25 | 30 | 30 | 30 | 30 | 30 | 12 | 30 | 12 | 30 | 30 | 30 | 30 | 30 |
| Jet Cooker & Column Passes | 1 | 1 | 1 | 1 | 1 | 1 | 1 | 1 | 1 | 1 | 1 | 2 | 3 | 1 | 2 |

[a]See Example 2.
[b]The-spray-dryer was fitted with a centrifugal wheel atomization nozzle.
[c]See Example 3, Part A.
[d]A stainless steel packing obtained from Nutter Engineering, Tulsa, Oklahoma.
[e]In a taste panel evaluation of a 5% solids dispersion in distilled water, 10/15 panelists preferred the 25% feed solids sample over a control sample of the same dextrin that had not been steam-striped. The same panelists identified the steam-stripped sample as being more bland than the control.

TABLE II

Bleached Steam-stripped Starch Hydrolysates

| Run: | Converted Tapioca Dextrin[a] Bleached[f], 10 foot column, B1-400 Packing[c], Spray-dried[d] | | | Converted Potato Maltodextrin[a,e], Bleached (2) and Unbleached (1), spray-dried[d] | | Debranched Waxy Maize Starch[f], Bleached 10 foot column, B1-400 Packing[g], Spray-dried[d] |
|---|---|---|---|---|---|---|
| Batch | 16 | 17 | 18 | 1 | 2 | 1 |
| Column Feed Solids (%) | 25 | 29 | 25 | 26 | 26 | 25 |
| Feed Rate (ml/min) | 225 | 275 | 275 | 275 | 275 | 0.26 gal/min/ft²[f] |
| Steam Flow (lb/hour) | 30 | 30 | 30 | 30 | 30 | 30 |
| Column Temp °C. (°F.) | 190 (275) | 190 (275) | 190 (275) | 190 (275) | 190 (275) | 90 (194) |
| Pressure (psi) | 30 | 30 | 30 | 30 | 30 | 30 |

[a]See Example 3, Part B.
[b]See Example 2.
[c]A stainless steel packing obtained from Nutter Engineering, Tulsa, Oklahoma.
[d]The spray-dryer was fitted with a centrifugal wheel atomization nozzle.
[e]In a taste panel evaluation of a 5% solids dispersion in distilled water, 12/16 panelists identified the steam-stripped (batch "1") potato maltodextrin as being more bland and preferred over a control sample of the same dextrin that had not been steam-stripped.
[f]See Example 3, Part C. The feed rate is expressed in gallons/minute/square foot area of column cross-section.
[g]The B1-200 Packing (stainless steel) was obtained from Nutter Engineering, Tulsa, Oklahoma.

EXAMPLE 3

Part A Several batches of an oxidized (treated with sodium hypochlorite at 5% active chlorine, on a starch dry weight basis, to give a 40 WF fluidity starch) waxy maize fluidity starch were steam-stripped under conditions described in Table I and compared to a control that had not been steam-stripped. Flavor improvements were observed in each of the steam-stripped batches.

and comprising about 65% short chain amylose), spray-dried waxy maize starch was dispersed in water, heated to 90° C. (197° F.), bleached with 0.19% sodium chlorite at a pH of 3.0 to 3.5 for 1.5 hours in a teflon-coated vessel and steam-stripped under the conditions described in Table II. This product was compared to a control that had neither been bleached nor steam-stripped. Flavor improvements were observed in the steam-stripped sample.

TABLE III

Steam-stripped Polysaccharides

| Run: | OSAA Treated Waxy Maize Dextrin[d], Spray-Dried[e] | | | Locust Bean Gum[a], 4 Feet Column, Ring Packing[e] | Tamarind Gum Hydrolysate[b], 4 Feet Column, 4 mm Glass Beads Packing, Freeze-Dried | High Amylose Corn Starch[c], Spray-Dried[e] |
|---|---|---|---|---|---|---|
| Batch | 1 | 2 | 3 | 1 | 1 | 1 |
| Column Feed Solids (%) | 9 | 9 | 9 | 0.57 | 30 | 18 |
| Feed Rate (ml/min) | 225 | 225 | 225 | 35 | 4.5 | 125 |
| Steam Flow (lb/hour) | 30 | 30 | 30 | 35 (g/min) (at 100° C.) | 0.46 | 20 |
| Column Temp °C. (°F.) | 117.8 (244) | 116.7 (242) | 115.6 (240) | 100 (212) | 100(212) | 138 (282) |
| Pressure (psig) | 12 | 11 | 10 | 0 | 0 | 35 |

[a]See Example 3, Part D.
[b]See Example 3, Part E. A 30% solids slurry was batch-treated on a laboratory scale distillation apparatus.
[c]See Example 3, Part F.
[d]See Example 3, Part G.
[e]See Example 2.

Part B An alpha-amylase enzyme-converted potato maltodextrin (Paselli SA2 dextrin, obtained from Avebe Company, Veendam, Holland) was steam-stripped, with and without a preliminary bleaching treatment by the method of Example 1 under the conditions set forth in Table II. Flavor and color improvements relative to a control sample were observed in each of the steam-stripped samples. The bleached, steam-stripped potato maltodextrin was preferred. A taste panel found a 5% solids dispersion of the control maltodextrin to be musty, astringent, starchy and brown in comparison with the treated samples.

Part C An enzymatically debranched get-cooked and treated with 9.4% pullulanase, on a starch dry weight basis, at pH 5.0 and 58° to 60° C., to yield a product having a funnel viscosity of 10 to 14 seconds at 25° C. and 19% solids Part D Locust bean gum (obtained from National Starch and Chemical Company, Bridgewater, N.J.) was slurried at 2% solids in de-ionized water and jet-cooked (as in Example 1) to 149° C. (300° F.). The resulting cooked gum dispersion at 0.95% solids was too viscous and was diluted with de-ionized water to 0.573% solids prior to steam-stripping.

The dispersed gum was fed into the 4 foot column, ring packed apparatus described in Example 2 and Table III at a flow rate of 36 ml/min, and a temperature of 88° C. (190° F.) against a current of steam flowing at a rate of 35 g/min at 100° C. Significant taste and odor improvements were observed in an aqueous gum dispersion by a six member taste panel that evaluated the steam-stripped gum against a control that had not been steam-stripped.

Part E A spray-dried, enzymatically-degraded (by treatment with a cellulase) tamarind seed gum (Glyloid gum, obtained from Dianippon Pharmaceuticals, Inc., Osaka, Japan) having a D.E. of 23.5 and a molecular weight of about 650 to 2,400, was dispersed in deionized water at 30% solids and steam-stripped under the conditions described in Table III to remove flavors, odors and colors.

The steam-stripped tamarind gum hydrolysate was freeze-dried, then reconstituted in water at 30% solids for organoleptic evaluation. Relative to a control, the steam-stripped tamarind gum hydrolysate had lost much of its characteristic beany flavor and odor, and was described as having a salty flavor with sweet afternotes and no reduction in color.

Part F An acid-converted (35 WF) high amylose (70% amylose) corn starch (Hylon VII starch, obtained from National Starch and Chemical Company, Bridgewater, N.J.) was slurried in deionized water at 20% solids and jet-cooked at 138° C. (218° F.). The cooked starch dispersion was steam-stripped under the conditions described in Table III. When used to prepare lemon pie filling, the steam-stripped starch was free of any objectionable aftertaste.

Part G An OSAA-treated (3%) pyrodextrin prepared from a waxy maize starch and having an ABF viscosity of 3.5 to 7.0 was steam-stripped under the conditions listed in Table II. Flavor and odor improvements were observed in the steam-stripped sample relative to a control.

EXAMPLE 4

This example illustrates the removal of off-flavors from an insoluble, granular starch by steam-stripping under vacuum at a temperature below the gelatinization temperature of the starch.

The apparatus of Example 2 is modified by connecting the steam exhaust orifice on the column to a vacuum pump of sufficient capacity to remove the steam feed. The vacuum is controlled with a regulator installed between the pump and the column. An additional pump is installed at the starch dispersion outlet on the bottom of the column.

In this low temperature process, granular starch is slurried in deionized water at 10 to 15% solids, preheated to 55° C. (131° F.) and fed into the column at a feed rate of 100–125 ml/min. The vacuum regulator and pumps connected to the column are adjusted to give a column pressure of −12.4 psig (12.4 psi of vacuum). The steam flow is adjusted to 30 to 100 lbs/hour.

The steam-stripped granular starch is recovered from the dispersion by spray-drying. The powdered, granular starch product is characterized by improved flavor and odor when used in foods and pharmaceutical products.

EXAMPLE 5

Dextrins were treated by the following activated carbon column process to improve color and flavor characteristics, with and without a preliminary bleaching treatment using the method of Example 1.

A. Carbon Pre-Wash

About 600 grams of activated carbon granules (CPG LF 12×40 obtained from Calgon Carbon Corporation, Pittsburgh, Pa.) were wetted with about 2,000 ml of polished water (filtered on a ion-exchange column and on an activated carbon column) in a 4,000 ml beaker. The water and surface carbon fines were decanted, leaving the carbon granules submerged in water. The carbon granules were rinsed with aliquots of an excess of polished water until the water became clear when swirled around the granules.

B. Column Preparation

A gasket and a 300 micron screen were placed on the bottom of a jacketed glass column, 36 inches (91 cm) in height (1 inch (2.54 cm) internal diameter), and the bottom was capped with an inlet/outlet port and an inlet/outlet valve. The washed carbon granules were rinsed from the beaker into the column through a funnel placed at the top of the column until the carbon granules reached a height of 18 inches (46 cm) within the column. The carbon was kept submerged in water at all times and excess water was drained while filling the column. A gasket and a 300 micron screen were placed on the top of the column and the column was capped with an inlet/outlet port, sample valve, pressure gauge and an inlet/outlet valve.

C. Column Back-Wash

A pump was connected to the valve at the bottom of the column and an inlet line to the pump was placed in a 5 gallon (18.9 liter) pail of polished water. An outlet line connected the valve at the top of the column to a drain. The sample valve was closed, the bottom and top inlet/outlet valves were opened and water was pumped into the bottom of the column at initial rate fast enough to remove any trapped air bubbles. The rate was lowered to allow the carbon to settle in the column, then the rate was increased to provide expansion of the carbon column to 125 to 150 percent of its resting height.

The back-washing was continued until the carbon had been washed with 100 bed volumes of polished water (about 23–24 liters). The back-washing was discontinued and the carbon permitted to stand (wetted) for 24 hours. The column was heated to 65° C., back-flushed with 65° C. polished water to remove trapped air, and the pump was disconnected from the bottom of the column. The pump was connected to the valve at the top of the column.

D. Sample Treatment

A total of 1,000 grams of dextrin (a canary tapioca pyrodextrin) were slurried in 3,000 ml polished water and jet-cooked at 300° F. (150° C.) with 65 psi (4.57 Kg/cm$^2$) inlet steam pressure. The dispersed dextrin sample was held in a boiling water bath and an inlet line to the pump on the column was placed into the sample. The pump was set at a flow rate of 3 bed volumes/hour and the dispersed dextrin was pumped through the carbon column. Aliquots (about 100 ml) of dispersed dextrin were collected from the bottom of the column and visually evaluated. Of the 23 aliquots examined, none contained visible, detectable fines. The dextrin dispersions were clear, without the gray color normally associated with carbon treatment, and were lighter, less yellow/brown than a control dextrin dispersion. The emulsification of carbon fines normally observed in carbon-treated starch or dextrin dispersions was absent following this treatment.

A 29 Kg sample of dextrin (a pregelatinized, alpha-amylase converted, tapioca dextrin, having a DE of 1 to 3) was dispersed in 80 liters polished water and jet-cooked at 275° C. and 60 psi (4.22 Kg/cm$^2$) inlet steam pressure. The dispersed dextrin was held in a boiling water bath prior to and during the column carbon treatment and treated samples were collected and held in a boiling water bath, filtered on diatomaceous earth, then spray-dried. No carbon fines were detected in the treated samples before or after filtration with diatomaceous earth.

Dextrin color, odor and flavor were improved by the activated carbon column treatment.

A dextrin sample described in Table I, below, was treated by the process described in Table I and subjected to organoleptic evaluation in a 10% dispersion in distilled water at a pH of 3.9.

TABLE I

ORGANOLEPTIC EVALUATION OF CARBON-TREATED DEXTRINS

| Sample[a] | Treatment | Color | Flavor | Odor |
|---|---|---|---|---|
| Tapioca dextrin | Control | Dark yellow, slightly cloudy | strong, caramel, rubber-like, objectionable aftertaste | strong, burnt dextrin |
| Tapioca dextrin | Carbon column[b] | Lighter yellow, clear | mild, dry, paper-like little aftertaste | very mild, starchy |

[a] A canary tapioca dextrin.
[b] The method of Example 5 was used to treat the dextrin, except that 8,000 grams of dextrin were dispersed in 14 liters of water; 18 linear inches of carbon were loaded into a 40" by 2" glass column; and 100 bed volumes (93–95 liters) of water were used to back-wash the column. The dextrin was spray-dried after treatment.

The results show that the column carbon treatment employed herein yielded an improved dextrin, having bland, non-objectionable flavor and color characteristics.

EXAMPLE 6

Soluble starch hydrolysates were treated by the bleaching method of Example 1, followed by ultrafiltration to improve color and flavor characteristics.

In the bleaching step, 1,000 g of a dextrinized OSAA treated (3%) waxy maize starch having an ABF value of 4 was dispersed in 3,000 mls of distilled water and jet-cooked at 149° C. (300° F.). This dextrin dispersion was filtered hot through diatomaceous earth (200 g of Celite 503 filter aid coated on a 32 cm Buchner funnel) and placed in a boiling water bath. When the temperature of the dispersion had equilibrated at 85° to 95° C., 0.2% sodium chlorite (on a dextrin dry weight basis) was added to the dextrin and bleaching was carried out for about 2 minutes. The completion of the oxidation was confirmed with a colorimetric potassium iodide spot test for residual chlorine and 0.05 g of sodium metabisulfite was added to the dispersion to ensure removal of any residual active chlorine.

The bleached dextrin dispersion was next ultrafiltered by feeding the dispersion at 20% solids into a Millipore Prolab Benchtop System (obtained from Millipore Corporation, Bedford, Mass.) equipped with an Amicon® 10,000 MWCO membrane (obtained from Amicon Division, W.R. Grace & Company, Beverly, Mass.). The volume of feed was maintained constant with a reserve of 10 liters of distilled water and the bleached dextrin was ultrafiltered at 25° C. and 45–50 psi pressure.

Because many dextrin contaminants are present in salt form, the progress of the ultrafiltration purification was monitored by measuring the conductivity of the dispersion being filtered. When the conductivity of the dispersion within the ultrafiltration unit had dropped to 100 μohms/cm, the ultrafiltration was discontinued. The permeate volume was 10,000 mls.

The bleached, ultrafiltered dextrin dispersion was freeze-dried and the purified dextrin recovered in powdered form.

The purified dextrin was dispersed at 10% solids in water at pH=4 and evaluated by a taste panel. The purified dextrin was lighter in color than the control and the panel readily observed a flavor improvement compared to the control that had not been bleached nor ultrafiltered.

The same panel found slight flavor improvements in an experimental sample that had been filtered with a 10,000 MWCO filter relative to an experimental sample filtered with a 30,000 MWCO filter, which in turn, was slightly improved relative to an experimental sample filtered with a 100,000 MWCO filter. All experimental samples had better flavor and color characteristics than the control that had not been bleached, nor ultrafiltered.

EXAMPLE 7

This example illustrates the removal of off-flavors, odors and colors from a dextrin using a combination of ultrafiltration and steam-stripping processes.

An octenylsuccinic acid anhydride (3% treatment) derivative of waxy maize starch that had been dextrinized (treated with acid under dry heat conditions) to yield a 4 ABF dextrin is dispersed in a 1:3 ratio in distilled water. The dispersion is jet-cooked at 149° C. (300° F.), then is filtered hot through diatomaceous earth (200 grams of Celite 503 filter aid coated on a 32 cm Buchner funnel). The pH is adjusted to 4.0 and the cooked dispersion is fed at 14% solids into the ultrafiltration apparatus described in Example 6 and diafiltered using a 30,000 molecular weight cut-off polysulfone spiral wound ultrafiltration membrane cartridge. The temperature is maintained at 50° C. and the pressure at 50 psi. The filtration is continued until the permeate level reaches 10,000 mls (from a sample prepared from 1,000 grams of starch plus 3000 mls of water).

The retentate from the ultrafiltration step is next fed into the 10 foot column steam-stripping apparatus of Example 2, fitted with Monz B1-400 packing. The retentate is fed at 14% solids at a flow rate of 225 ml/min at 190° C. (275° F.) under 30 psig steam pressure against a steam flow of 30 lb/hour. The product is spray-dried.

The product is characterized by improved flavor and color and lower salt content than a control that has not been ultrafiltered and steam-stripped.

EXAMPLE 8

This example illustrates the removal of off-flavors, odors and colors from enzyme-degraded tamarind gum (treated with cellulase to yield a gum D.E. of 23–26) by a combination of bleaching, ion exchange and carbon treatments.

The degraded gum (1000 g) is dispersed in 3000 mls of polished water and the pH is adjusted to 8.8 with a 3% sodium hydroxide solution. The dispersed gum is filtered through diatomaceous earth (40 g of Celite 503 filter aid on a 24 cm Buchner funnel) and the pH is lowered to 6.5 with a 3:1 hydrochloric acid solution.

The gum in the filtrate is bleached with 68 g of a 30% hydrogen peroxide solution for 2 hours. The bleached gum dispersion is fed at a rate of 57 ml/min onto a 2.54 cm (1") internal diameter, 91.44 cm (36") high column packed with 400 mls of Amberlite® IRA 400 anion exchange resin (obtained from Rohm and Haas Company, Philadelphia, Pa.) that had been charged with a 3% sodium hydroxide solution and rinsed with copious amounts of water. The effluent is then fed at a rate of 57 ml/min onto a 2.54 cm (1") internal diameter, 91.44 cm (36") high column packed with 400 mls of Amberlite® 200 cation exchange resin (obtained from Rohm and Haas Company, Philadelphia, Pa.) that had been charged with 3:1 hydrochloric acid and rinsed with copious amounts of water.

The ion exchange effluent is then fed at a rate of 57 mls/min onto a 2.54 cm (1") internal diameter, 91.44 cm (36") high column packed with 400 mls of Cecicarb 1240+ activated carbon (obtained from Atochem Company, Pryor, Okla.) that had been rinsed with copious amounts of water. The purified gum dispersion is recovered by freeze-drying. The purified, depolymerized gum in powdered form is dispersed in water for evaluation. The purified gum is characterized by the absence of off-flavor and a lighter color when compared to a control gum that had not been purified.

EXAMPLE 9

White sauces were prepared using the soluble starch hydrolysates (dextrins) of this invention and evaluated for flavor and color.

The following white sauce formulation was used.

| | White Sauce Formulation | | |
|---|---|---|---|
| | Dextrin Addition | | |
| Ingredient | 1% (g) | 2% (g) | 4% (g) |
| Butter | 28.38 | 56.00 | 56.00 |
| Flour | 13.04 | 20.20 | 8.40 |
| Salt | 1.35 | 2.70 | 2.70 |
| Milk | 250.00 | 500.00 | 500.00 |
| Dextrin | 2.96 | 11.80 | 23.60 |

Sauces were prepared by melting the butter over low heat, blending in the flour and dextrin for 3–5 minutes, adding the milk and salt and cooking with stirring until the sauce thickened.

The dextrin used in the white sauce was an OSAA treated (3% on a starch dry weight basis) waxy maize starch that had been converted to an anhydrous Borax fluidity (ABF) viscosity of 3.5 to 7.0 by pyrodextrinization. The control dextrin had not been treated by the process of this invention. A sample of the dextrin (described in Table III and Example 3, Part G) had been steam-stripped by the process of Example 2 prior to use in the white sauce. The control dextrin had not been purified prior to use in the white sauce.

At the 1% and 2% dextrin usage levels, flavor and color improvements were not detected during organoleptic evaluations. At the 4% dextrin usage level, 9/10 taste panelists found the sauce made from the experimental dextrin to be more bland and cleaner in flavor than the control dextrin sauce and 10/10 taste panelists preferred the flavor of the sauce prepared from the experimental dextrin.

EXAMPLE 10

This example illustrates the removal of furfural from a dextrin using only steam stripping.

A low viscosity waxy maize starch that had been dextrinized (treated with acid under dry heat conditions) to an ABF value of 2 was slurried at 60% solids in distilled water and adjusted to a pH of 5.0 or 6.8 with sodium hydroxide. The dispersion was jet-cooked at 143° C. (290° F.) and steam-stripped using the procedure described in Example 2 except that the maximum steam pressure was 30 psi instead of 60 psi.

The furfural content of the dextrin was determined before purification and after steam-stripping to remove the volatiles. A Perkin Elmer model Sigman 2000 gas chromatograph was used. It was fitted with a J&W Scientific Model DB624 capillary column and a Perkin Elmer flame ionization detector. The sample was introduced to the column by a Perkin Elmer model HS-100 head space analyzer.

The ppm furfural (dry basis) are shown below.

| | Unpurified Dextrin | Jet-Cooked And Steam-Stripped Dextrin |
|---|---|---|
| pH 5.0 | 143 | 9 |
| pH 6.8 | 143 | 8 |

Steam stripping reduced the furfural level from 143 ppm to 9 ppm for the starch jet-cooked at pH 5.0 and to 8 ppm for the starch jet-cooked at pH 6.8. Thus, the steam stripping process removed about 95% of the furfural.

Thus, improved foods and adhesives may be prepared using the purified and deflavored dextrins of this invention.

We claim:

1. A process for purifying a soluble polysaccharide by removing undesirable flavors and/or odors which comprises the steps of:
   A) dispersing the soluble polysaccharide at 1 to 40% solids in an aqueous medium;
   B) feeding the dispersed polysaccharide into a steam-stripping apparatus;
   C) feeding a current of steam past the dispersed polysaccharide in the steam-stripping apparatus;
   D) removing the steam from the steam-stripping apparatus; and
   E) recovering the steam-stripped soluble polysaccharide from the aqueous dispersing medium.

2. The process of claim 1, wherein the polysaccharide dispersion is fed, at a temperature of 55° to 200° C. against a countercurrent of steam at 55° to 200° C. and 5 to 300 psig, into a steam-stripping column fitted with inert packing material at a flow rate of 0.03 to 3.75 gal/min/ft$^2$.

3. The process of claim 2, wherein temperature is 80° to 200° C. and the pressure is 10 to 40 psig.

4. The process of claim 1, further comprising one or more process steps, carried out after the steam-stripping steps and before the recovery step, which are selected from the group consisting of:
   A) bleaching the steam-stripped polysaccharide by bringing the polysaccharide into contact with a bleaching agent selected from the group consisting of peroxides and ozone;
   B) feeding the steam-stripped polysaccharide into an ultrafiltration apparatus fitted with a membrane having a molecular weight cutoff minimum of 1,000 and recovering the filtered polysaccharide retained by the ultrafiltration membrane, with the proviso that, if the recovered filtered polysaccharide is to be subjected to another step, the polysaccharide is redispersed at 1 to 40% solids in an aqueous medium;

C) passing the steam-stripped polysaccharide through at least one column packed with pre-washed, granular, activated carbon at a flow rate of 0.1 to 20.0 bed volumes/hour, which column is loaded with wetted carbon granules, back-washed and pre-heated; and/or D) feeding the steam-stripped polysaccharide at a flow rate of 0.001 to 10.0 gal/min/ft$^2$ into an ion exchange apparatus.

5. The process of claim 1, further comprising one or more process steps, carried out before the steam-stripping step and after the dispersing step, which are selected from the group consisting of:

A) bleaching the dispersed polysaccharide by bringing the polysaccharide into contact with a bleaching agent selected from the group consisting of chlorite salts, hypochlorite salts, peroxides, persulfate salts, permanganate salts, chlorine dioxide and ozone for a period of time sufficient to improve the color of the polysaccharide without substantial degradation of the polysaccharide;

B) feeding the dispersed polysaccharide into an ultrafiltration apparatus fitted with a membrane having a molecular weight cutoff minimum of 1,000, recovering the filtered polysaccharide retained by the ultrafiltration membrane, and redispersing the recovered polysaccharide at 1 to 40% solids in an aqueous medium;

C) passing the dispersed polysaccharide through at least one column packed with pre-washed, granular, activated carbon at a flow rate of 0.1 to 20.0 bed volumes/hour, which column is loaded with wetted carbon granules, back-washed and pre-heated; and/or D) feeding the dispersed polysaccharide at a flow rate of 0.001 to 10.0 gal/min/ft$^2$ into an ion exchange apparatus.

6. The process of claim 1, further comprising the step of bleaching the dispersed polysaccharide by bringing the polysaccharide into contact with a bleaching agent selected from the group consisting of chlorite salts, hypochlorite salts, peroxides, persulfate salts, permanganate salts, chlorine dioxide and ozone for a period of time sufficient to improve the color of the polysaccharide without substantial degradation of the polysaccharide.

7. A process for treating a soluble polysaccharide with activated carbon which comprises the steps of:

A) dispersing the polysaccharide in an aqueous medium at 40% solids;

B) passing the dispersed polysaccharide through at least one column packed with pre-washed, granular, activated carbon at a flow rate of 0.1 to 20.0 bed volumes/hour, which column is loaded with wetted carbon granules, back-washed and pre-heated; and C) recovering the activated carbon treated polysaccharide in a form which is substantially free of carbon fines.

8. The process of claim 7, wherein the soluble polysaccharide is a starch or a starch hydrolysate and wherein the flow rate is 0.2 to 3.0 bed volumes/hour.

9. The process of claim 8, wherein the soluble polysaccharide is a starch hydrolysate having a DE of 20 or less.

10. The process of claim 9, wherein the starch hydrolysate has a DE of 10 or less.

11. The process of claim 7, further comprising the step of:

A) bleaching the dispersed polysaccharide, before the activated carbon treatment, with a bleaching agent selected from the group consisting of chlorite salts, hypochlorite salts, peroxides, persulfate salts, permanganate salts, chlorine dioxide and ozone for a period of time sufficient to improve the color of the polysaccharide without substantial degradation of the polysaccharide; and/or B) bleaching the activated carbon treated polysaccharide with a bleaching agent selected from the group consisting of peroxides and ozone.

12. The process of claim 7, further comprising one or more of the steps of:

A) feeding the dispersed or the activated carbon treated polysaccharide at a flow rate of 0.001 to 10.0 gal/min/ft$^2$ into an ion exchange apparatus; and/or B) feeding the dispersed or the activated carbon treated polysaccharide into an ultrafiltration apparatus fitted with a membrane having a molecular weight cutoff minimum of 1000, recovering the filtered polysaccharide retained by the membrane, and, if a subsequent step is to be carried out, redispersing the filtered polysaccharide in an aqueous medium at 1 to 40% solids.

13. The process of claim 12, further comprising the step(s) of:

A) bleaching the dispersed polysaccharide, before the ion exchange treatment or before the ultrafiltration, with a bleaching agent selected from the group consisting of chlorite salts, hypochlorite salts, peroxides, persulfate salts, permanganate salts, chlorine dioxide and ozone for a period of time sufficient to improve the color of the polysaccharide without substantial degradation of the polysaccharide;

B) bleaching the ion exchange treated polysaccharide with a bleaching agent selected from the group consisting of peroxides and ozone; and/or C) bleaching the filtered polysaccharide with a bleaching agent, selected from the group consisting of peroxides and ozone, after recovery of the polysaccharide retained by the ultrafiltration membrane and redispersion of the filtered polysaccharide in an aqueous medium of 1 to 40% solids.

14. A process for purifying a soluble polysaccharide selected from the group consisting of starch(es), gum(s), dextrin(s), cellulose(s) and hetereopolysaccharide(s), and derivatives thereof; starch hydrolysates having a DE of 20 or less; and combinations thereof, by removing undesirable flavors and/or odors from the polysaccharide; which comprises the steps of:

A) dispersing the soluble polysaccharide in an aqueous medium at 1 to 40% solids;

B) feeding the dispersed polysaccharide into an ultrafiltration apparatus fitted with a membrane having a molecular weight cutoff minimum of 1,000; and C) recovering the filtered soluble polysaccharide retained by the ultrafiltration membrane.

15. The process of claim 14, further comprising the steps of:

A) bleaching the dispersed polysaccharide, before the ultrafiltration, with a bleaching agent selected from the group consisting of chlorine salts, hypochlorite salts, peroxides, persulfate salts, permanganate salts, chlorine dioxide and ozone for a period of time sufficient to improve the color of the polysaccharide without substantial degradation of the polysaccharide;

B) bleaching the filtered polysaccharide, after recovery from the ultrafiltration membrane and redispersion of the filtered polysaccharide in an aqueous medium at 1 to 40% solids, with a bleaching agent selected from the group consisting of peroxides and ozone and recovering the bleached product; and/or C) feeding the filtered polysaccharide, after redispersion in an aqueous medium at 40% solids, into an ion exchange apparatus at a low rate of 0.001 to 10.0 gal/min/ft$^2$ and recovering the ion exchanged polysaccharide.

16. A process for purifying a soluble polysaccharide selected from the group consisting of starch(es), gum(s), dextrin(s), cellulose(s) and hetereopolysaccharide(s), and derivatives thereof; starch hydrolysates having a DE of 20 or less; and combinations thereof, by removing undesirable flavors and/or odors from the polysaccharide; which comprises the steps of:

A) dispersing the soluble polysaccharide in an aqueous medium at 1 to 40% solids;

B) feeding the dispersed polysaccharide into an ion exchange apparatus at a flow rate of 0.001 to 10.0 galmin/ft$^2$; and C) recovering the ion exchange-treated soluble polysaccharide.

17. The process of claim 16, further comprising the step(s) of:

A) bleaching the dispersed polysaccharide, before the ion exchange treatment with a bleaching agent selected from the group consisting of chlorite salts, hypochlorite salts, peroxides, persulfate salts, permanganate salts, chlorine dioxide and ozone for a period of time sufficient to improve the color of the polysaccharide without substantial degradation of the polysaccharide; and/or B) bleaching the ion exchange treated polysaccharide with a bleaching agent selected from the group consisting of peroxides and ozone.

18. A process for purifying a water insoluble polysaccharide by removing undesirable flavors and/or odors which comprises the steps of:

A) slurrying the insoluble polysaccharide at 1 to 40% solids in an aqueous medium;

B) feeding the slurried polysaccharide into a steam-stripping apparatus;

C) feeding a current of steam past the slurried polysaccharide in the steam-stripping apparatus;

D) removing the steam from the steam-stripping apparatus; and

E) recovering the steam-striped insoluble polysaccharide from the aqueous slurry medium.

19. The process of claim 18, wherein the slurried polysaccharide has a viscosity of less than 300 cps and is fed, at a temperature of 25° to 80° C. against a countercurrent of steam at 55° to 200° C. and −5 to −14.5 psig, into a steam-stripping column fitted with inert material at a flow rate of 0.03 to 3.75 gal/min/ft$^2$.

20. The process of claim 4, wherein the temperature is 55° to 80° C. and the pressure is −10 to −14.5 psig.

* * * * *